(12) United States Patent
Colli

(10) Patent No.: US 8,368,123 B2
(45) Date of Patent: Feb. 5, 2013

(54) APPARATUS FOR SENSING AN EVENT

(75) Inventor: Alan Colli, Cambridgeshire (GB)

(73) Assignee: Nokia Corporation, Espoo (FI)

( * ) Notice: Subject to any disclaimer, the term of this patent is extended or adjusted under 35 U.S.C. 154(b) by 169 days.

(21) Appl. No.: 12/645,959

(22) Filed: Dec. 23, 2009

(65) Prior Publication Data

US 2011/0147802 A1 Jun. 23, 2011

(51) Int. Cl.
*H01L 29/78* (2006.01)
(52) U.S. Cl. .......................... 257/253; 257/213; 257/157
(58) Field of Classification Search .................. 257/157, 257/213, 253
See application file for complete search history.

(56) References Cited

U.S. PATENT DOCUMENTS

| | | | |
|---|---|---|---|
| 7,485,908 B2 * | 2/2009 | Anwar et al. | 257/296 |
| 7,786,086 B2 * | 8/2010 | Reches et al. | 530/300 |
| 7,902,089 B2 * | 3/2011 | Matsumoto et al. | 438/791 |
| 8,022,393 B2 * | 9/2011 | Colli | 257/24 |
| 2006/0081886 A1 * | 4/2006 | Mostarshed et al. | 257/213 |
| 2006/0263255 A1 * | 11/2006 | Han et al. | 422/83 |
| 2007/0134866 A1 * | 6/2007 | Huang et al. | 438/199 |
| 2007/0262344 A1 * | 11/2007 | Anwar et al. | 257/157 |
| 2008/0009434 A1 * | 1/2008 | Reches et al. | 514/2 |
| 2008/0063566 A1 * | 3/2008 | Matsumoto et al. | 422/68.1 |
| 2008/0221806 A1 * | 9/2008 | Bryant et al. | 702/22 |
| 2010/0025658 A1 * | 2/2010 | Colli | 257/24 |

OTHER PUBLICATIONS

A.M. Ward, et al., *Annuals of Clinical Biochemistry*, "Prostate specific antigen: biology, biochemistry and available commercial assays," vol. 38, 633 (2001) (abstract only).

C. Campganolo, et al., *Journal of Biochemistry and Biophysical Methods*, "Real-Time, label-free monitoring of tumor antigen and serum antibody interactions," J. Biochem. Biophys. Methods 61, 283-298 (2004).
S.F. Chou, et al., *Biosens. Bioelectron*, "Development of an immunosensor for human ferritin, a nonspecific tumor marker, based on surface plasmon resonance," vol. 19, 999-1005 (2004).
P. Alivisatos, *Nat. Biotechnol*, "The use of nanocrystals in biological detection," vol. 22, 47-52 (2004).
J.M. Nam, et al., *Science*, "Nanoparticle-Based Bio-Bar Codes for the Ultrasensitive Detection of Proteins," vol. 301, 1884-1886 (2003).
G. Wu, et al., *Nature. Biotechnology*, "Bioassay of prostate-specific antigen (PSA) using microcantilevers," vol. 19, 856-860 (2001).
RJ. Chen, et al., *Journal of American Chemical Society*, "An Invenstigation of the Mechanisms of Electron Sensing of Protein Adsorbtion on Carbon Nanotube Devices," vol. 126, 1563-1568 (2004).
Y. Cui, et al., *Science*, "Nanowire Nanosensors for Highly Sensitive and Selective Detection of Biological and Chemical Species," vol. 293, 1289-1292 (2001).

(Continued)

*Primary Examiner* — Marc Armand
*Assistant Examiner* — Bilkis Jahan
(74) *Attorney, Agent, or Firm* — Harrington & Smith

(57) ABSTRACT

A sensor configured to sense an external event including: a first component having a first impedance that changes when the external event occurs and being connected between a reference voltage node and an output node wherein the output node is configured to provide, when the external event occurs, a feedback signal to the first component that further changes the first impedance and wherein the first component is a field effect transistor comprising: a gate formed from a conductive core of a nanowire and connected to the output node; a gate dielectric formed from an insulating shell of the nanowire; a source/drain electrode connected to the output node; a source/drain electrode connected to the reference node; and a channel extending between the source/drain electrodes.

20 Claims, 3 Drawing Sheets

OTHER PUBLICATIONS

Hahm, et al., *Nano Letters*, "Direct Ultrasensitive Electrical Detection of DNA and DNA Sequence Variations using Nanowire Nanosensors," vol. 4, 51-54 (2004).

Z. Li, et al., *Nano Letters*, "Sequence-Specific Label-Free DNA Sensors based on Silicon Nanowires," vol. 4, 245-247 (2004).

G. Zheng, et al., *Nature Biotechnology*, "Multiplexed electrical detection of cancer markers with nanowire sensor arrays," vol. 23, 1-8 (2005).

W. Chen, et al., *Applied Physics Letter*, "Silicon nanowires for high-sensitivity glucose detection," 88, 213104-1, 3 pages (2006).

P. Bergveld, *IEEE Trans. Biomedical Engineering*, "Development, Operation, and Application of the Ion-Sensitive Field-Effect Transistor as a Tool for Electrophysiology," BME-19, 342-351 (1972).

D.G. Hafeman, et al., *Science*, "Light-Addressable Potentiometric Sensor for Biochemical Systems," vol. 240, 1182-1185 (1988).

E. Stern, et al., *Nature*, "Label-free immunodetection with CMOS-compatible semiconducting nanowires," vol. 445, 519-522 (2007).

J. Wan, et al., "Silicon nanowire sensor for gas detection fabricated by nanoimprint on SU8/SiO2/PMMA trilayer," *Microelectric Engineering 86*, 1238-1242 (2009).

F. Patolsky, et al., "Fabrication of silicon nanowire devices for ultrasensitive, label-free, real-time detection of biological and chemical species," *Nature Protocols 1*, 1711-1724 (2006).

F. Patolsky, CM. Lieber, *Materials Today*, "Nanowire Nanosensors," 20-28 (Apr. 2005).

Colli, A. Fasoli, et al., *Nano Letters*, "Nanowire lithography on silicon," vol. 8, 1358-1362 (2008).

A. Colli, et al., *Journal of Applied Physics*, "Thermal and chemical vapor deposition of Si nanowires: Shape control, dispersion, and electrical properties," 102, 034302-1, 13 pages (2007).

X. Duan, et al., *Nature*, "Indium Phosphide Nanowires as Building Blocks for Nanoscale Electronic and Optoelectronic Devices," vol. 409, 66-69 (2001).

Y. Huang, et al., *Nano Letters*, "Gallium Nitride Nanowire Nanodevices" vol. 2, No. 2, 101-104 (2002).

SJ. Tans, et al., "Room-temperature transistor based on a single carbon nanotube," *Nature 393*, 49-52 (1998).

R. Martel, et al., *Applied Physics Letters*, "Single- and multi-wall carbon nanotube field-effect transistors," vol. 73, 2447-2449 (1998).

Zhou, J. Kong, H. Dai, *Applied Physics Letters*, "Electrical measurements of individual semiconducting single-walled carbon nanotubes of various diameters," vol. 76, 1597-1599 (2000).

Y. Cui, CM. Lieber, *Science*, "Functional nanoscale electronic devices assembled using silicon nanowire building blocks," 291, 851-853 (2001).

Y. Huang, X. Duan, Y. Cui, L. J. Lauhon, K. H. Kim, and C. M. Lieber, "Logic gates and computation from assembled nanowire building blocks," *Science*, vol. 294, No. 5545, pp. 1313-1317 (2001).

V. Derycke, R. Martel, J. Appenzeller, and Ph. Avouris, "Carbon Nanotube Inter- and Intramolecular Logic Gates," *Nano Letters* 1, 453-456 (2001).

A. Bachtold, P. Hadley, T. Nakanishi, C. Dekker; *Science*, "Logic circuits with carbon nanotube transistors," vol. 294, Issue 5545, 1317-1320 (2001).

CR. Barrett, The Digital Evolution, *MRS Buletin*, "The Digital Evolution," 31, 906-913 (2006).

X. Duan, Y. Huang, and C. M. Lieber , Nonvolatile Memory and Programmable Logic from Molecule-Gated Nanowires, *Nano Letters 2*, 487-490 ( 2002).

Y. Li, Y. Bando, and D. Goldberg, *Advanced Materials*, "Indium-Assisted Growth of Aligned Ultra-Long Silica Nanotubes," 16,No. 1, 37-40 (2004).

S. Kawasaki, et al., *Appl. Phys. Lett*, "Conformal oxide coating of carbon nanotubes," 92, 053109-1, 3 pages (2008).

L.J. Lauhon, M.S. Gudiksen, D. Wang and C.M. Lieber, "Epitaxial core-shell and core-multi-shell nanowire heterostructures," *Nature*, vol. 420, 57-61 (2002).

R. Fan, Y. Wu, D. Li, M. Yue, A. Majumdar, and P. Yang, *Journal Am. Chem. Soc*, "Fabrication of silica nanotubes from vertical silicon nanowire array," 125, 5254-5255 (2003).

F. Qian, Y. Li, S. Gradecak, D. Wang, C.J. Barrelet and C.M. Lieber, "Gallium Nitride-Based Nanowire Radial Heterostructures for Nanophotonics," *Nano Letters* 4, 1975-1979 (2004).

Y. Dong, G. Yu, M.C. McAlpine, W. Lu and C.M. Lieber, "Si/a-Si Core/Shell Nanowires as Nonvolatile Crossbar Switches," *Nano Letters* 8, 386-391 (2008).

F. Qian, S. Gradecak, Y. Li, C-Y. Wen, CM. Lieber, "Core/multishell nanowire . . . high-efficiency light-emitting diodes", *Nano Letters* 5, 2287-2291 (2005).

W.S. Yun, et al., "Fabrication of metal nanowire using carbon nanotube as a mask," *Sci. Technol*. 18, 1329-1333 (2000).

R. Sordan, M. Burghard, and K. Kern, "Removable template route to metallic nanowires and nanogaps," *Appl. Phys. Lett*. 79, 2073-2075 (2001).

M.G. Ancona, et al., "Patterning of Narrow Au Nanocluster Lines Using V2O5 Nanowire Masks and Ion-Beam Milling," *Nano Lett*. 3, 135-138 (2003).

S. Myung, K. Heo, M. Lee, Y-H. Choi, S-H. Hong, S. Hong, *Nanotechnology*, "'Focused' assembly of V2O5 nanowiremasks for the fabrication of metallic nanowire sensors," 18, 205304-1, 4 pages (2007).

D. Whang, S. Jin and C. M. Lieber, "Nanolithography Using Hierarchically Assembled Nanowire Masks," *Nano Lett*. 3, 951-954 (2003).

Colli, A. Tahraoui, A. Fasoli, J. Kivioja, A.C. Ferrari, "Dual-gate silicon nanowire ransistors in a single fabrication step", ACS Nano 3, 1587-1593 (2009).

\* cited by examiner

APPARATUS FOR SENSING AN EVENT

FIELD OF THE INVENTION

Embodiments of the present invention relate to sensors. In particular, they relate to nano-scale sensors.

BACKGROUND TO THE INVENTION

The principal figure of merit used to characterize a sensor is its sensitivity (S), defined as $$S = \Delta I / I_0$$

where $I_0$ is the current flowing through the sensor and $\Delta I$ the current variation due to a sensing event.

Nano-scale devices typically function with currents in the nA range. Sophisticated measurement setups are thus needed to discriminate variations in conductivity of only a few percents and minimize other sources of noise that could overshadow detection events (light, vibrations, thermal drift, etc.).

BRIEF DESCRIPTION OF VARIOUS EMBODIMENTS OF THE INVENTION

According to various, but not necessarily all, embodiments of the invention there is provided a sensor configured to sense an external event comprising: a first component having a first impedance that changes when the external event occurs and being connected between a reference voltage node and an output node wherein the output node is configured to provide, when the external event occurs, a feedback signal to the first component that further changes the first impedance and wherein the first component is a field effect transistor comprising: a gate formed from a conductive core of a nanowire and connected to the output node; a gate dielectric formed from an insulating shell of the nanowire; a source/drain electrode connected to the output node; a source/drain electrode connected to the reference node; and a channel extending between the source/drain electrodes.

According to various, but not necessarily all, embodiments of the invention there is provided a sensor arrangement configured to sense an event comprising: a first reference voltage node connected to a first component having a first impedance; a second reference voltage node connected to a second component having a second impedance; an output node via which the first component and second component are serially connected wherein the relative difference between the first impedance and the second impedance changes when the event occurs and the output node is connected to provide, when the event occurs, a feedback signal to at least the first component that further changes the relative difference between the first impedance and the second impedance and wherein the first component is a field effect transistor comprising: a gate formed from a conductive core of a nanowire and connected to the output node; a gate dielectric formed from an insulating shell of the nanowire; a source/drain electrode connected to the output node; a source/drain electrode connected to the second reference node; and a channel extending between the source/drain electrodes.

According to various, but not necessarily all, embodiments of the invention there is provided a method comprising: masking the substrate using a nanowire comprising a conductive core and an insulating shell; performing an anisotropic etch that selectively etches the substrate in favor of the insulating shell to form a raised channel underlying the nanowire; selectively etching a portion of the insulating shell of the nanowire to expose a portion of the conductive core of the nanowire; and depositing conductive interconnect to form an interconnect contacting the exposed portion of the conductive core of the nanowire and a portion of the raised channel.

Some embodiments of the invention provide local upscaling of a signal level to a range that could be read by some sort of compact, cheap and portable electronic readout, as would be the case for a sensor embedded in a mobile personal device.

Some embodiments of the invention integrate some level of signal processing (including the relatively simple case of amplification) into a nano-scale sensor.

BRIEF DESCRIPTION OF THE DRAWINGS

For a better understanding of various examples of embodiments of the present invention reference will now be made by way of example only to the accompanying drawings in which.

DETAILED DESCRIPTION OF VARIOUS EMBODIMENTS OF THE INVENTION

Figure 1:
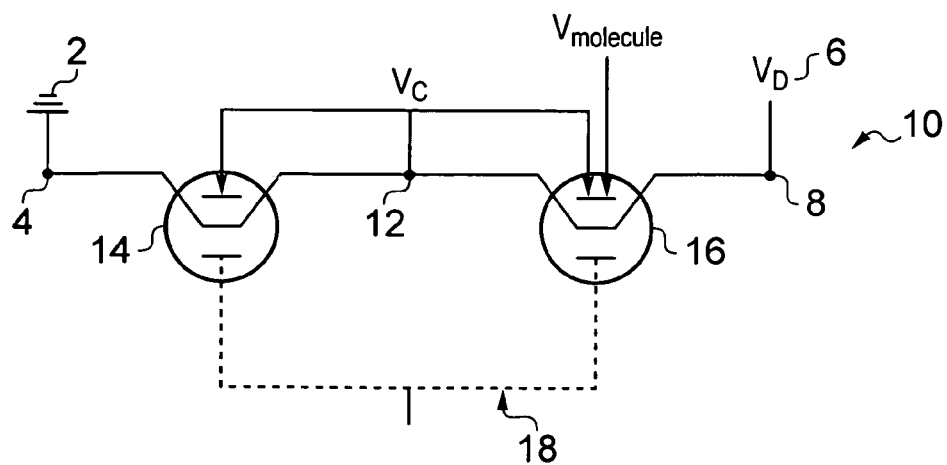
FIG. 1 schematically illustrates an example of a sensor arrangement.

FIG. 1 schematically illustrates a sensor arrangement 10 configured to sense an event. The sensor arrangement 10, in this example, comprises a first component 16 and a second component 14.

The first component 16 has a first impedance (resistance). It is connected between a first reference voltage node 8 and an output node 12.

The second component 14 has a second impedance (resistance). It is connected between and the output node 12 and a second reference voltage node 4, different to the first reference voltage node 8.

In this example, the first reference voltage node 8 is held at a first constant voltage $V_D$. The second reference voltage node 4 is held at a second constant voltage (Ground). The sensor arrangement therefore operates as a voltage divider, dividing the voltage $V_D$ across the first component 16 and the second component 14 in proportion to their respective resistances. The divided voltage is measurable at the output node 12.

The sensor arrangement 10 is arranged so that when a particular external event occurs the difference between the first resistance and the second resistance changes. This relative change in resistance results in a change in the output voltage $V_C$ at the output node 12 which will change the electric current through the series connected first component 16 and second component 14. The occurrence of the external event can therefore be detected.

The ease with which an external event can be detected can be improved by configuring the sensor arrangement 10 so that there is self-amplification or positive feedback. The output node 12 is connected to provide, when the external event occurs, a feedback signal to at least one of the first and second components 14, 16. This feedback signal further changes the relative difference between the first resistance and the second resistance setting up a self-amplifying feedback loop.

It is of course important to ensure that the first resistance and the second resistance do not vary in the same manner when an external event occurs as the net result would be no change in the output voltage $V_C$ at the output node 12. Such a differential response may, for example, be achieved by using different components for the first and second components. Alternatively, the same components could be used for the first and second components but the external event could be prevented from affecting one of the components but not the other of the components. In this example, one of the first resistance and the second impedance is variable in response to an external event and the other is invariant in response to the external event.

The first component 16 in this illustrated example is a first field effect transistor (FET). The second component 14 in this illustrated example is a second field effect transistor. The source/drain nodes of the first and second field effect transistors are interconnected via the output node 12. Likewise the gates of the first and second field effect transistors are interconnected via the output node 12. Optionally a common bottom gate 18 may be used.

Figure 2A:
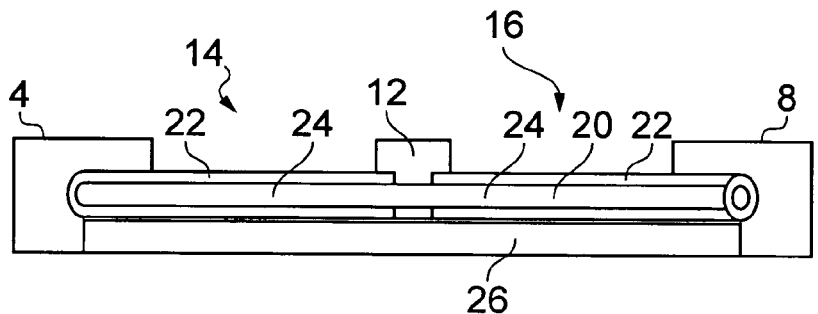
FIG. 2A schematically illustrates an example of an 'integrated' sensor arrangement.

FIG. 2A schematically illustrates an 'integrated' sensor arrangement in which the first field effect transistor 16 and the second field effect transistor 14 share a common gate electrode. The common gate is formed from a conductive core 24 of a nanowire 20 and a gate dielectric is formed from an insulating exterior shell or coating 22 of the nanowire 20. The insulating shell 22 is absent in the vicinity of the output node 12.

The nanowire 20 overlies a channel 26. In this example, the channel 26 is a raised channel that has exposed side walls and also a top surface carrying the nanowire 20. The nanowire 20 is a nanostructure aligned with the channel which is also a nanostructure. A nanostructure is a structure with at least one physical dimension less than 1 µm.

A source/drain 4 of the second FET 14 is formed from interconnect over a peripheral portion of the nanowire 20 and the underlying channel 26. As the conductive core 24 of the nanowire is surrounded by the insulating shell 22, the interconnect contacts only the insulating shell 22 of the nanowire and does not contact the conductive core 24. As the channel is exposed at this portion (exposed side walls) the interconnect contacts the channel 26 and forms a peripheral source/drain terminal for the second FET 14.

Another source/drain 12 of the second FET 14 is formed from interconnect over a central portion of the nanowire 20 and the underlying channel 26. The insulating shell 22 is absent from this portion of the nanowire 20. As the conductive core 24 of the nanowire is not surrounded by the insulating shell 22 at this portion, the interconnect contacts the conductive core 24. As the channel is exposed at this portion (exposed side walls) the interconnect also contacts the channel 26 and forms a central source/drain terminal for the second FET 14. This interconnect operates as the output node 12 connecting the gate 24 and source/drain 12 of the second FET 14.

As the first FET 16 and the second FET 14 use a common nanowire to form their gates and a common raised structure to form their channels, the interconnect that forms a central source/drain terminal for the second FET 14 also forms a central source/drain terminal for the first FET 16. This interconnect operates as the output node 12 connecting the gate 24 and source/drain 12 of the first FET 16.

A peripheral source/drain 8 of the first FET 16 is formed from interconnect over another peripheral portion of the nanowire 20 and the underlying channel 26. As the conductive core 24 of the nanowire is surrounded by the insulating shell 22, the interconnect contacts only the insulating shell 22 of the nanowire and does not contact the conductive core 24. As the channel is exposed at this portion (exposed side walls) the interconnect contacts the channel 26 and forms a peripheral source/drain terminal for the first FET 16.

A first FET channel extends between the peripheral source/drain node 8 of the first FET 16 and the central source/drain terminal of the first FET 16 that is shared with the second FET 14. The first FET channel may be engineered to have a particular channel impedance response when an external event occurs. The conductive core of the nanowire gates a whole of the first FET channel.

A second FET channel extends between the peripheral source/drain node 4 of the second FET 14 and the central, shared source/drain terminal of the second FET 14. The second FET channel may be engineered to have a particular channel impedance response when an external event occurs. The conductive core of the nanowire gates a whole of the second FET channel.

The first and second FETs are engineered so that when an external event occurs there is a differential change in the conductivities (impedances) of the FET channels. This may be achieved by enabling an external event to modify the conductivity of one of the FET channels but not the other FET channels by for example preventing the external event affecting one of the FET channels but not the other FET channel or by enabling an external event to modify the conductivity of both of the FET channels but by different amounts and/or in different senses. This may, for example, be achieved by having differential FET characteristics. For example, one FET channel may have a different concentration or type of doping in its channel compared to the other FET channel. As another example, one FET channel may a different cross-sectional area compared to the other FET channel.

An external event is an event that occurs at the exterior of the sensing arrangement 10. It excludes changes to the operating conditions of the sensing arrangement 10 such as changes to applied voltage or current. It includes events that interface with the sensing arrangement 10 via one or more FET channels. Typically an external event is an external physical event that involves the interaction of quanta with the channel. The quanta may, for example, include photons, molecules, chemical species, biological species etc. The quanta may in some instances be a fluid, be part of a fluid or be carried in a fluid.

It has been found that some chemical or biological species change the conductivity of a nano-scale FET channel when they contact the FET channel. It is believed that the species bind to the FET channel and alter the conductivity of the FET channel. Examples include $NO_2$ and Streptavidin.

The presence of an exposed sidewall to the FET channel increases the surface area available to the species for binding.

The detection of chemical and biological species is a critical issue for many areas of healthcare and medical science, ranging from the diagnosis of diseases to the discovery and screening of new drug molecules.

Selective recognition of a biological or chemical species of interest may be achieved by using specifically designed receptors attached to the FET channel. A sensor arrangement 10 with specific sensing capabilities is achieved by linking a recognition group to the surface of the FET channel. Biological macromolecules, such as proteins and nucleic acids, are typically charged in aqueous solution and, as such, can be detected readily when appropriate receptors are linked to the FET channel surface. A silicon channel 26 with its natural oxide coating makes this receptor linkage straightforward since extensive data exists for the chemical modification of silicon oxide or glass surfaces from planar chemical and biological sensors.

The following documents, for example, provide examples of how to bind chemical or biological receptors on the surface of nanowire devices.

J. Hahm and C. M. Lieber, *Nano Lett.* 4, 51 (2004)
G. Zheng, F. Patolsky, Y. Cui, W. U. Wang, and C. M. Lieber, *Nat. Biotechnol.* 23, 1294 (2005)
W. Chen, H. Yao, C. H. Tzang, J. Zhu, M. Yang, S. T. Lee, *Appl. Phys. Lett.* 88, 213104 (2006)
E. Stern, J. F. Klemic, D. A. Routenberg, P. N. Wyrembak, D. B. Turner-Evans, A. D. Hamilton, D. A. LaVan, T. M. Fahmy, M. A. Reed, Nature 445, 519 (2007)

Gas sensors or very basic chemical sensors (e.g., PH sensors) do not need specific functionalization. That is, the as-fabricated device without specific receptors will work properly when exposed to a charged or polar gaseous environment (e.g., $NH_3$).

The sensing arrangement 10 may be modified to operate in a liquid environment by completely passivating the terminals with an inert insulating layer to avoid shorting of the terminals through an ionized solution.

Organic receptors can be destroyed or corrupted by the device fabrication process, and may be attached after the fabrication process is complete, including any passivation.

The FET channel may be operated close to pinch off (e.g. to maximize $M_D$ for any $\Delta V_G$ caused by the absorption/binding of chemical species). This ensures that the channel resistance at the operating point dominates over the contact resistance, which can thus be neglected.

Figure 2B:
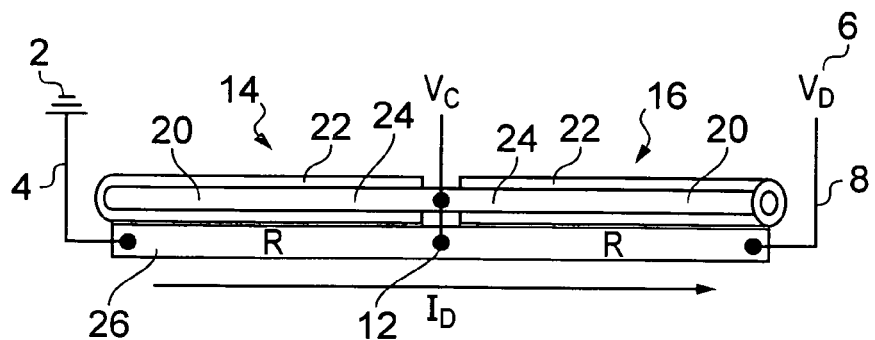
FIG. 2B schematically illustrates an example of the 'integrated' sensor arrangement in use.

Referring to FIG. 2B, the central terminal 12 divides the channel 26 into two sections. Let the first FET 16 have a channel resistance $R_1$ and the second FET 14 have a channel resistance $R_2$. When absorption/binding of chemical species occurs a label * is used to indicate the parameters. Assuming that $R_2$ is not allowed to change with the environment and that only $R_1$ will respond to a binding event, and the following equations will apply:

before binding:

$$V_C = R_2 I_D$$

$$V_D - V_C = R_1 I_D$$

after binding:

$$V_C^* = R_2 I_D^*$$

$$V_D - V_C^* = (R_1 + \Delta R) I_D^*$$

which leads to (taking into account that $V_D = (R_1+R_2)I_D = (R_1+R_2+\Delta R)I_D^*$):

$$V_C = \frac{V_D}{2} + \frac{V_D}{2}\frac{(R_2 - R_1)}{(R_2 + R_1)}$$

$$V_C^* = \frac{V_D}{2} + \frac{V_D}{2}\frac{(R_2 - \Delta R - R_1)}{(R_2 + \Delta R + R_1)}$$

Therefore, we eventually get the general formula for $\Delta V_C$:

$$\Delta V_C = V_C^* - V_C = -\frac{I_D^* \Delta R}{2}\left(\frac{2R_2}{R_2 + R_1}\right)$$

Since it is desirable to maximize $\Delta V_G$, the factor $\alpha = 2R_2/(R_2+R_1)$ must also be maximized. We note that $\alpha$ is maximum ($\alpha\sim 2$) when $R_2 \gg R_1$, whereas $\alpha$ can become very small ($\alpha\sim 2R_2/R_1$) if $R_2 \ll R_1$. A suitable design for a sensor arrangement may avoid situations when $R_1$ is greater than $R_2$.

When the first FET 16 senses the correct species in the environment, its resistance will change $R_1$ and as a consequence of the binding event, for fixed $V_D$, we will thus have modulation $\Delta V_C$ of the voltage at the output node 12:

Such modulation is applied via feedback to the gate of the first FET 16 which will cause a further change of the channel resistance. The first FET can be designed so that such further change is greater than $\Delta R$ and amplification of the sensing signal at the output node 12 is achieved.

Figure 2C:
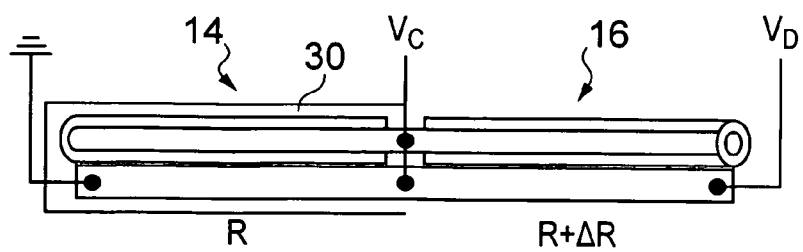
FIG. 2C schematically illustrates an example of a partially passivated 'integrated' sensor arrangement.

It is of course important to ensure that the first resistance and the second resistance do not vary in the same manner when an external event occurs as the net result would be no change in the output voltage $V_C$ at the output node 12. Such a differential response may, for example, be achieved by using the same components for the first and second components but the external event could be prevented from affecting one of the components but not the other of the components. FIG. 2C illustrates an example of this. It is the same sensor arrangement as illustrated in FIG. 2A, however, in this example the second FET 14 is embedded in a passivation layer 30. Suitable passivation layers include $SiO_2$ or SiN. The passivation layer can be prepared by means of a lithographic method once the whole sensor arrangement is successfully fabricated.

However, any suitable means could additionally or alternatively be used to generate an asymmetric potential drop that would lead to a finite $\Delta V_C$. For example, one may use a tapered nano-scale channel 26, i.e., a channel with variable diameter. The section with the largest diameter will be less sensitive to the environment due to the lower surface-to-volume ratio. Another possibility is to prepare the two FET channels with slightly different doping concentrations. As a result, the two FET channels will operate as sensors with different operating points, and thus their response will be asymmetric. In particular, the channel of the second FET 14 may have a lower doping concentration so the condition R2>R1 is fulfilled.

FIG. 3 schematically illustrates a method suitable for creating the sensor arrangement 10 illustrated in FIG. 2A.

The method is a nano-scale fabrication method that uses nanowire lithography (NWL). This is a self-aligned, easy and cheap fabrication process.

The first stage is the fabrication of the nano-scale channel 26.

A substrate 40 is masked using a nanowire 20. The nanowire comprises a conductive core 24 and an insulating shell 22.

The nanowire may, for example, be a silicon nanowire grown by vapor-transport, either by Au-seeded or oxide-assisted growth. These silicon nanowires which are originally synthesized as single-crystalline structures, are then covered in $SiO_2$ by furnace annealing in $O_2$ atmosphere. A relatively thin (~5 nm) oxide shell 22 forms around the crystalline silicon thus leaving a protected core 24 available as active element. The final silicon nanowires have lengths up to several microns and diameters between 30 and 50 nm.

The substrate 40 is a heterostructure comprising a first upper portion and a second underlying portion.

The two portions have different properties. Typically the first upper portion is more conductive than the second underlying portion. The heterostructure may be formed from semiconductor on insulator (SOI) or from a locally doped monolithic semiconductor wafer. The substrate may be thin (30-100 nm). Silicon is a suitable semiconductor material. Alternative semiconductor materials may include germanium, zinc oxide or graphene.

An anisotropic etch is performed that selectively etches the substrate 40 in favor of the insulating shell 22. The anisotropic etch is continued through the first upper portion of the substrate 40 into the second underlying portion creating a raised channel 26 from the first upper portion of the substrate 40. Deep-reactive-ion-etching (DRIE) is suitable for etching single-crystalline Si. The high Si-to-$SiO_2$ selectivity of the DRIE process (Si is etched very efficiently while $SiO_2$ is almost unaffected) means that a thin $SiO_2$ shell 22 retains very well its masking function even for Si etching depths of several microns.

Figure 3A:
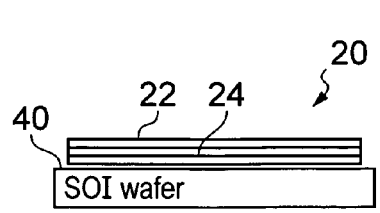
FIG. 3 schematically illustrates an example of a method suitable for creating the sensor arrangement illustrated in FIG. 2A.

The resulting structure is illustrated in FIG. 3A.

Figure 3B:
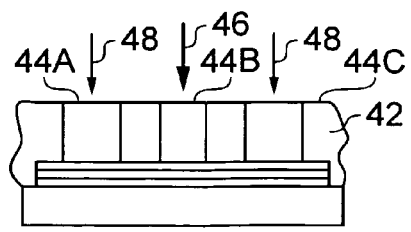
Figure 3C:
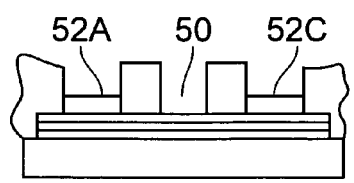
Figure 3D:
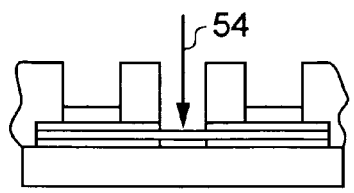

The next stage is the selective etching of a portion of the insulating shell 22 of the nanowire 20 to expose a central portion of the conductive core 25 of the nanowire 20. This may be achieved by depositing a resist 42 over the substrate 40 and the nanowire 20 (FIG. 3B). The resist is selectively removed from a first central area to expose the central portion of the insulating shell 22 (FIG. 3C). Then selectively etching 54 of the central portion of the insulating shell 22 occurs (FIG. 3D).

Figure 3E:
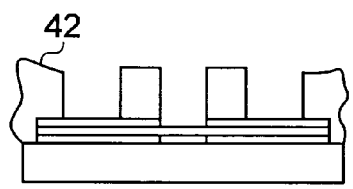

Then the resist is selectively removed from a second peripheral area to expose the insulating shell 22 and the raised channel 26 of the substrate 40 and also from and a third peripheral area to expose the insulating shell 22 and the raised channel 26 of the substrate 40 (FIG. 3E). The first central area is positioned between the second peripheral area and the third peripheral area.

Conductive interconnect is then deposited at the first central area to form an interconnect contacting the exposed portion of the conductive core 24 of the nanowire 20 and a portion of the raised channel 26 of the substrate 40. This forms the output node 12 as a central terminal.

Conductive interconnect is deposited at the second peripheral area to form an interconnect contacting the insulating shell 22 of the nanowire 20 and a portion of the raised channel 26 of the substrate 40. This forms a peripheral terminal.

Conductive interconnect is deposited at the third peripheral area to form an interconnect contacting the insulating shell 22 of the nanowire 20 and a portion of the raised channel 26 of the substrate 40. This forms a peripheral terminal.

The conductive interconnect may be metal.

The formation of the central terminal is different to the formation of the peripheral terminals because at the central terminal it is necessary to additionally etch locally the shell 22 around the nanowire 20 prior to deposition of the conductive interconnects. The shell 22 at the peripheral terminals prevents shortage between the gate and source/drain.

Double-dose lithography may be used to fabricate the terminals in a single step. An example of this process follows:

A polymethyl methacrylate (PMMA) resist layer 42 is spun on top of the substrate 40 and the nanowire 20 and exposed under the electron beam using two different doses. The resist layer 42 may be 500-nm-thick.

In this example, a high dose (HD) 46 is used in the first central area 44B where the central terminal will be defined and a low dose (LD) 48 is used in the second peripheral area 44A and the third peripheral area 44C where the peripheral terminals will be defined. An example of a high dose is 1.0-1.2 $mC/cm^2$. An example of a low dose is 0.6-0.8 $mC/cm^2$ The resist layer 42 is then developed in an methyl-isobutyl-ketone:2-propanol (MIBK:IPA) 1:3 solution for 20 sec. These conditions ensure the HD pattern is fully developed, while the LD features are left partially undeveloped. Thus, as illustrated in FIG. 3C, the resist layer 42 is removed 50 from the first central area where the central terminal will be defined and is retained, at least partially as masks 52A, 52B, in the second peripheral area and the third peripheral area where the peripheral terminals will be defined.

The exposed oxide shell 22 in the central area is etched 54 using buffered HF (buffered oxide etching, BOE) which is used to strip away the oxide shell 22. The residual resist layer 52A, 52C masks and protects the second peripheral area and the third peripheral area where the peripheral terminals will be defined.

The resist layer 42 is then developed more aggressively in a stronger developer e.g. methyl-isobutyl-ketone:2-propanol (MIBK:IPA) 1:1. These conditions ensure the LD pattern is fully developed. Thus, as illustrated in FIG. 3E, the resist layer 42 is removed from the second peripheral area and the third peripheral area where the peripheral terminals will be defined.

Figure 3F:
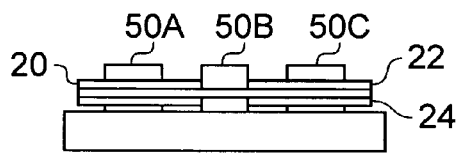

Finally, metal (Ni, Cr, Ti, Al, Au, etc.) is evaporated to form the peripheral terminal (isolated from the core 24 of the nanowire 20) and the central terminal, which shorts locally the channel 26 and the core 24 of the nanowire 20. The resist is then removed as illustrated in FIG. 3F.

By this method, the central terminal has a finite length limited by the lithographic resolution. The effectiveness of the device will benefit if such length is made as small as possible in comparison with the whole FET channel length.

The core 24 of the nanowire 20 is capable of gating the whole FET channel while leaving the sidewalls of the FET channel exposed to the environment, and thus available for sensing. This is not the case for a conventional FET where the channel is embedded, isolating it from the species to be sensed.

The second underlying portion of the substrate 40 (not shown) can be used as a back gate to set the FET operating point.

Using a core-shell nanowire 20 as mask enables a powerful bottom-up method to precisely align two isolated and "active" nanostructures on top of each other for their whole length. This is achieved without the need for conventional lithography nor assembly or manipulation at the nano-scale. The top nanostructure plays the role of a top gate of one or more FETs and the bottom nanostructure forms one or more FET channels.

The above described method creates two FETs that use a common nanowire 20 as a common gate. The process may be modified to create instead a single FET. For example, if the process were adapted not to form the second peripheral terminal, then a single FET would result. This may be achieved by retaining the resist at the second peripheral area 44C until after the metal deposition.

Such 'isolated' as opposed to integrated FETs may however be joined in series via metal interconnect or similar. Sensing may be enabled in one of the FETs but not the other.

Figure 4:
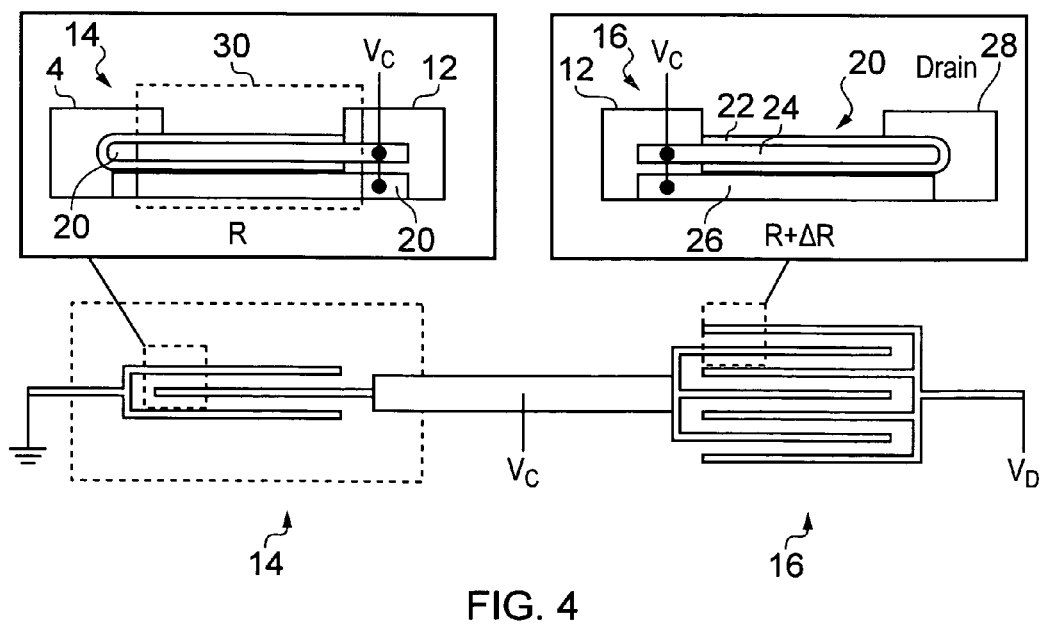
FIG. 4 schematically illustrates an example of a 'non-integrated' sensor arrangement.

For example, referring to FIG. 4, two interdigitated FET devices 14, 16 are placed at an arbitrary distance (which makes very easy the selective passivation of one of them) and are connected by a large scale central metallic terminal, which at both FET devices is in contact both with the FET channel and the FET gate. Since any potential drop along such metallic contact can be neglected (the resistance of the FET channels is much higher), the entire large scale central metallic contact and all the gates (on both sides) will be at potential $V_C$. The operating principle for the device will thus be the same as that illustrated in FIG. 2A. Note that the asymmetric interdigitated pattern illustrated has less parallel FETs for the left "inactive" device, which will fulfill the condition $R_2>R_1$.

Figure 5:
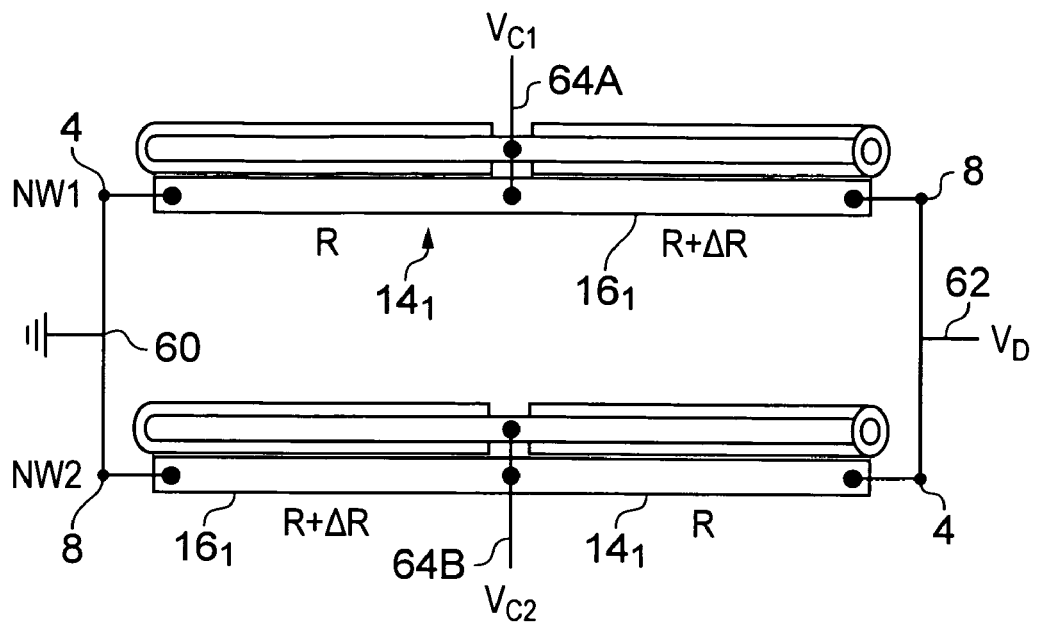
FIG. 5 schematically illustrates an example of a differential or complementary sensing arrangement.

To discriminate false-positive events during sensing (due to, e.g., light, vibrations, thermal drift, etc.), a differential or complementary sensing arrangement may be used such as the example illustrated in FIG. 5.

Two sensor arrangements are connected in parallel. The sensor arrangements operate in a complimentary or differential fashion. That is, for example, the voltages at the output nodes 12 of the sensor arrangements change in response to a sensing event in opposite directions e.g. one increases while the other decreases. There is consequently a significant difference in the differential voltage between the output nodes of the sensor arrangements.

Referring to FIG. 5, the first reference voltage node 8 of the first sensor arrangement is electrically connected to the second reference voltage node 4 of the second sensor arrangement at a common node 62 held at a first constant voltage $V_D$. The first reference voltage node 8 of the second sensor arrangement is electrically connected to the second reference voltage node 4 of the first sensor arrangement at a common node 60 held at a second constant voltage (Ground). The output node of the first sensor arrangement provides a first output terminal 64A. The output node of the second sensor arrangement provides a second output terminal 64B. The output terminals 64A, 64B provide a differential output signal.

In this example, the first FET 16 of the first sensor arrangement and the second sensor arrangement have the same doping and are both exposed for sensing. The second FET 16 of the first sensor arrangement and the second sensor arrangement are passivated and are not exposed for sensing.

In an alternative embodiment, the first FET 16 of the first sensor arrangement and the second FET 14 of the second sensor arrangement have channels of opposite conductivity (p or n) and are both exposed for sensing. The second FET 14 of the first sensor arrangement and first FET 16 of the second sensor arrangement are passivated and are not exposed for sensing.

Figure 6:
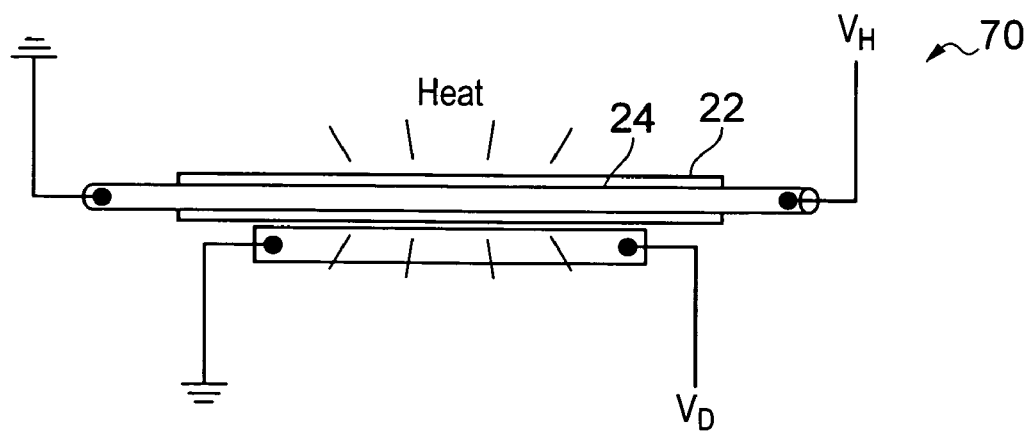
FIG. 6 schematically illustrates an example of a resistive heater.

As illustrated in FIG. 6, the conductive core 24 of the nanowire 20 may be used as a resistive heater.

Maximum sensitivity may be achieved above room temperature. To avoid the huge dissipation and power consumption necessary to heat up the whole sample, a local heater may be used to bring a sensor arrangement to the best operating temperature.

The nanowire 20 may also be used as a local heater. The nanowire 20 may have a metallic core 24. Possible examples include $SiO_2$-coated metallic carbon nanotubes or $NiSi/SiO_2$ core/shell nanowires. Since the core 24 is metallic and contacted independently from the sensor circuit, a small $V_H$ is sufficient for a high current to flow in the core 24, thus locally providing significant heat. As $V_H \ll V_D$, the top-gating effect could be made negligible (or purposefully introduced, according to need).

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

I claim:

1. A sensor configured to sense an external event comprising:
    a first component having a first impedance that changes when the external event occurs and being connected between a reference voltage node and an output node
    wherein the output node is configured to provide, when the external event occurs, a feedback signal to the first component that further changes the first impedance and wherein the first component is a field effect transistor comprising:
    a gate formed from a conductive core of a nanowire and connected to the output node;
    a gate dielectric formed from an insulating shell of the nanowire; a source/drain electrode connected to the output node; a source/drain electrode connected to the reference node; and a channel, formed by nanowire lithography, exrending between the source/drain electrodes;
    wherein the conductive core of the nanowire is metallic and functions as a resistive heater.

2. A sensor as claimed in claim 1, wherein, when the external event occurs, the feedback signal is positive or self-amplifying feedback signal.

3. A sensor as claimed in claim 1, wherein the conductive core of the nanowire gates a whole of the channel.

4. A sensor as claimed in claim 1, wherein the channel is a nanostructure and the gate is a nanostructure aligned with the channel.

5. A sensor as claimed in claim 1, wherein the channel is raised and has exposed sidewalls.

6. A sensor as claimed in claim 1, wherein the field effect transistor is configured such that the external event varies a conductivity of the channel.

7. A sensor as claimed in claim 1, wherein the external event is the presence of a chemical or biological species in contact with the field effect transistor.

8. A sensor as claimed in claim 7, wherein the field-effect transistor comprises receptors for the species.

9. A sensor as claimed in claim 1, wherein the external event comprises a binding of a chemical or biological species to an exposed sidewall of the channel of the field effect transistor.

10. A sensor arrangement configured to sense an event comprising:
    a sensor as claimed in claim 1; and
    a second component having a second impedance connected between a second reference voltage node, different to the first reference voltage node, and the output node;
    wherein the relative difference between the first impedance and the second impedance changes when the external event occurs and wherein the output node is configured to provide, when the external event occurs, a feedback signal to at least the first component that further changes the relative difference between the first impedance and the second impedance.

11. A sensor arrangement as claimed in claim 10, wherein the second component is a field effect transistor comprising:
- a gate formed from a conductive core of a nanowire and connected to the output node;
- a gate dielectric formed from an insulating shell of the nanowire;
- a source/drain electrode connected to the output node;
- a source/drain electrode connected to the second reference node; and
- a second channel extending between the source/drain electrodes.

12. A sensor arrangement as claimed in claim 11, wherein the first component and the second component share a common nanowire that extends from the first component via the output node to the second component.

13. A sensor arrangement as claimed in claim 12, wherein the insulating shell of the common nanowire is absent at the output node.

14. A sensor arrangement as claimed in claim 10, wherein there is an asymmetry between the first component and the second component that results in a different change in impedance in response to an event.

15. An apparatus comprising:
a first and a second sensor arrangement as claimed in claim 10; wherein the first reference voltage node of the first sensor arrangement is electrically connected to the second reference voltage node of the second sensor arrangement and wherein the first reference voltage node of the second sensor arrangement is electrically connected to the second reference voltage node of the first sensor arrangement and wherein the output node of the first sensor arrangement and the output node of the second sensor arrangement provide a differential output signal.

16. A sensor as claimed in claim 1, wherein the conductive core of the nanowire is used as a local heater.

17. A sensor as claimed in claim 16, wherein the conductive core of the nanowire is configured to heat the sensor arrangement.

18. A sensor as claimed in claim 16, wherein the reference voltage is held at a first voltage and the conductive core of the nanowire is provided with a second voltage; and
wherein the first voltage is significantly larger than the second voltage.

19. A sensor as claimed in claim 18, wherein the gating effect from the second voltage is negligible.

20. A sensor as claimed in claim 1, wherein the channel is formed by nanowire lithography using the nanowire.

* * * * *

UNITED STATES PATENT AND TRADEMARK OFFICE
CERTIFICATE OF CORRECTION

| | |
|---|---|
| PATENT NO. | : 8,368,123 B2 |
| APPLICATION NO. | : 12/645959 |
| DATED | : February 5, 2013 |
| INVENTOR(S) | : Colli |

Page 1 of 1

It is certified that error appears in the above-identified patent and that said Letters Patent is hereby corrected as shown below:

Claim 11, col. 11, line 15 after channel insert -- , formed by nanowire lithography, --.

Signed and Sealed this
Second Day of April, 2013

Teresa Stanek Rea
*Acting Director of the United States Patent and Trademark Office*